United States Patent
Ito

(10) Patent No.: US 11,957,738 B1
(45) Date of Patent: Apr. 16, 2024

(54) WATER SOLUBLE COMPOSITION AND PRODUCTION METHOD THEREOF

(71) Applicant: GEIHOKU PHARMACY CO., LTD, Hiroshima (JP)

(72) Inventor: Koichi Ito, Hiroshima (JP)

(73) Assignee: GEIHOKU PHARMACY CO., LTD, Hiroshima (JP)

( * ) Notice: Subject to any disclaimer, the term of this patent is extended or adjusted under 35 U.S.C. 154(b) by 0 days.

(21) Appl. No.: 18/525,147

(22) Filed: Nov. 30, 2023

Related U.S. Application Data

(63) Continuation of application No. PCT/JP2021/046291, filed on Dec. 15, 2021.

(51) Int. Cl.
*A61K 38/40* (2006.01)
*A61K 33/00* (2006.01)
*A61K 33/06* (2006.01)
*A61P 1/02* (2006.01)

(52) U.S. Cl.
CPC .............. *A61K 38/40* (2013.01); *A61K 33/00* (2013.01); *A61K 33/06* (2013.01); *A61P 1/02* (2018.01)

(58) Field of Classification Search
CPC ........... A61K 38/46; A61K 7/16; A61Q 11/00
USPC ........................................... 424/49
See application file for complete search history.

(56) References Cited

U.S. PATENT DOCUMENTS

| 5,898,037 A | 4/1999 | Marx |
| 2003/0003059 A1* | 1/2003 | Dana ................. A61K 8/986 424/49 |
| 2012/0034280 A1 | 2/2012 | Cohen et al. |
| 2018/0117070 A1 | 5/2018 | Kawase |

FOREIGN PATENT DOCUMENTS

| JP | 2007-223975 A | 9/2007 |
| JP | 2013-538199 A | 10/2013 |
| JP | 2016-175901 A | 10/2016 |
| JP | 2016-210758 A | 12/2016 |
| JP | 2018-043982 A | 3/2018 |
| WO | WO2016/174861 * | 3/2016 ............... A23L 2/52 |

OTHER PUBLICATIONS

Kondo et al., "Effects of oral administration of bovine lactoferrin on periodontitis patients" Jun. 2008.
Kobayashi et al. "Effects of ingestion of lactoferrin on periodontal disease patients" Sep. 2011.
Komatsu, et al., "Present and Future of Bittern Industry with Focus on Bromine" 1980.

* cited by examiner

*Primary Examiner* — Walter E Webb
(74) *Attorney, Agent, or Firm* — Maschoff Brennan

(57) ABSTRACT

A water-soluble composition for bacteriostasis or for absorption through mucosal tissue which improves a cellular environment and a production method thereof are provided. The water-soluble composition contains magnesium, sodium, and protein. A content ratio between the magnesium and the sodium is magnesium:sodium=16:1 to 73:1. The protein is lactoferrin. A percentage content of the magnesium is 8.0 w/v % to 12.0 w/v %. A percentage content of the lactoferrin is 3.0 w/v % to 10.0 w/v %.

3 Claims, 8 Drawing Sheets

FIG.6

| SYMPTOMS | BEFORE START OF TEST | AFTER THREE MONTHS |
|---|---|---|
| ANNOYED BY BAD BREATH | 4 | 2 |
| STICKINESS AND SLIMINESS | 3 | 3 |
| TEETH WOBBLE | 2 | 2 |
| LOOSE TOOTH DIFFICULTY IN CHEWING HARD FOOD | 2 | 2 |
| POOR GUM COLOR | 6 | 4 |
| GUMS SOMETIMES SWELL | 3 | 3 |
| BLEEDING GUM | 5 | 3 |
| GINGIVAL RECESSION | 2 | 2 |
| INCREASE IN GAP BETWEEN TEETH | 2 | 2 |
| REPEATED STOMATITIS | 6 | 3 |

WATER SOLUBLE COMPOSITION AND PRODUCTION METHOD THEREOF

TECHNICAL FIELD

The present disclosure relates to a water-soluble composition and a production method thereof.

BACKGROUND ART

Periodontal disease has been recognized as a bacterial infection. Therefore, various oral compositions having a bactericidal effect have been proposed as means for ameliorating periodontal disease.

For example, Patent Document 1 discloses an oral composition containing a cationic bactericide such as cetylpyridinium chloride.

CITATION LIST

Patent Document

Patent Document 1: Japanese Unexamined Patent Publication No. 2018-043982

SUMMARY OF THE INVENTION

Technical Problem

In the oral cavity, there are so-called good bacteria (probiotics) that regulate the oral environment. However, such highly bactericidal anti-periodontal oral compositions may destroy not only the bad bacteria but also the good bacteria. For oral care, it is unnecessary to kill good bacteria.

In recent years, it has been increasingly recognized that symptoms of periodontal disease are caused by the cellular environment of the periodontal tissues. The American Academy of Periodontology (AAP) has changed the category of periodontal disease from infectious disease to inflammatory disease. In order to effectively prevent periodontal disease, it is considered to be important not to sterilize the inside of the oral cavity but to provide a good oral environment in which good bacteria tend to increase.

Therefore, the present disclosure is intended to provide a water-soluble composition for improving the cellular environment and a production method thereof.

Solution to the Problem

<1> A water-soluble composition for bacteriostasis or for absorption through mucosal tissue, the composition contains magnesium; sodium; and protein,
 a content ratio between the magnesium and the sodium being magnesium:sodium=16:1 to 73:1,
 the protein being lactoferrin,
 a percentage content of the magnesium being 8.0 w/v % to 12.0 w/v %,
 a percentage content of the lactoferrin being 3.0 w/v % to 10.0 w/v %.
<2> The water-soluble composition for bacteriostasis or for absorption through mucosal tissue according to <1>, in which the percentage content of the magnesium is 10.5 w/v % to 12.0 w/v %, and the water-soluble composition is for oral use.
<3> A method for producing the water-soluble composition for bacteriostasis or for absorption through mucosal tissue according to <1>, the method comprising:
 preparing a sodium-containing magnesium solution with a content ratio between the magnesium and the sodium of magnesium:sodium=16:1 to 73:1;
 mixing lactoferrin and the sodium-containing magnesium solution to obtain a mixture solution with a percentage content of the magnesium of 8.0 w/v % to 12.0 w/v % and a percentage content of the lactoferrin of 3.0 w/v % to 10.0 w/v %; and
 defoaming the mixture solution.
<4> The method for producing the water-soluble composition for bacteriostasis or for absorption through mucosal tissue according to <3>, in which the percentage content of the magnesium is 10.5 w/v % to 12.0 w/v %.

According to the present disclosure, nutrients are absorbed through the mucosal tissue and supplied to the cells, thereby making it possible to improve the cellular environment and provide various effects. For example, an anti-inflammatory effect against bacterial inflammation is obtained. When the water-soluble composition of the present disclosure is used in oral compositions such as dentifrices and mouthwashes, the water-soluble composition can decrease the motility of bad bacteria in the mouth and improve the cellular environment in the gums, thereby making it possible to reduce inflammation and bleeding of the gums and prevent periodontal disease. When taken orally, the water-soluble composition of the present disclosure can reduce the motility of bad bacteria in the gastrointestinal tract and improve the cellular environment in the gastrointestinal tract, thereby making it possible to ameliorate constipation caused by a disorder in the balance between good and bad bacteria in the intestines, for example. In addition, when the water-soluble composition of the present disclosure is applied to wounded or burned skin, the water-soluble composition can facilitate amelioration of inflammation.

Advantages of the Invention

As described above, the present disclosure can provide a water-soluble composition that improves the cellular environment.

BRIEF DESCRIPTION OF THE DRAWINGS

FIG. 6 shows an example entry of a subjective evaluation check sheet used for evaluation of the water-soluble composition, which is an evaluation result of test subject 007.

FIG. 9 shows an example entry of an inspection table of a probing inspection, which is an inspection result of test subject 007 before the start of the test.

FIG. 10 shows an example entry of an inspection table of a probing inspection, which is an inspection result of test subject 007 after three months.

DESCRIPTION OF EMBODIMENT

Figure 1:
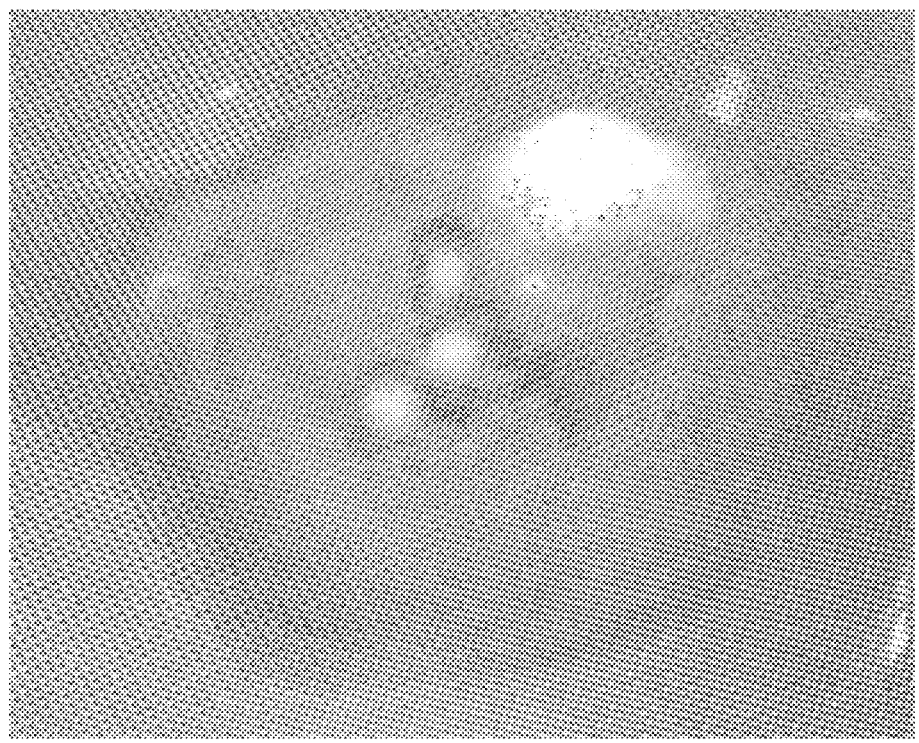
FIG. 1 is a photograph in foaming evaluation of a 2.0 w/v % lactoferrin preparation.

The embodiments will be described in detail below. The description of the preferred embodiments is illustrative only, and is not intended to limit applications or use of the water-soluble composition.

[Composition, Action, and Use]

The water-soluble composition of the present disclosure (hereinafter also merely referred to as a "composition") contains magnesium at a high concentration, sodium, and lactoferrin as a protein, and is absorbed through the mucosal tissue to supply nutrients to cells, thereby making it possible to improve the cellular environment and provide various effects.

[Magnesium]

Magnesium ions are abundant in cells and are one of the major minerals essential for life support. Deficiency of magnesium ions in cells is thought to deteriorate the cellular environment and causes various diseases. The composition allows magnesium to be absorbed through the mucosal tissue, thereby making it possible to improve the cellular environment and provide various effects.

In the water-soluble composition, the percentage content of the magnesium is preferably 2.0 w/v % to 12.0 w/v %, more preferably 8.0 w/v % to 12.0 w/v %, yet more preferably 8.5 w/v % to 12.0 w/v %, particularly preferably 9.0 w/v % to 12.0 w/v %, most preferably 10.5 w/v % to 12.0 w/v %. A remarkable effect is exhibited by blending magnesium in such percentage content. In this specification, "to" is used to mean that numerical values described before and after "to" are included as a lower limit and an upper limit.

The inventor thinks deficiency of magnesium is one of the causes that deteriorate the periodontal cell environment. Supplementation with magnesium is considered to be effective for alleviating various symptoms such as bleeding from gums and dissolution of alveolar bone caused by periodontal disease which is caused by deterioration of the periodontal cell environment. It is considered that magnesium in a high concentration of 9.0 w/v % or more acts more effectively on improvement of symptoms of periodontal disease, particularly bleeding from gums.

As magnesium, naturally derived high-concentration magnesium solution is preferable. As the naturally derived high-concentration magnesium solution, a readily commercially available solution can be used, which can be, for example, a 12.0 w/v % magnesium solution produced from the lake water of the Great Salt Lake, Utah, USA.

For oral compositions for prevention of periodontal disease, the preferable percentage content of the magnesium is 10.5 w/v % to 12.0 w/v %.

[Sodium]

Sodium can promote the effect of magnesium by being contained in the magnesium solution. In order to synergistically enhance the above effect of magnesium which improves the cellular environment, the content ratio between magnesium and sodium (hereinafter also referred to as a "Mg:Na ratio") is considered to be important. In order to obtain the effect of improving the cellular environment, the content ratio of magnesium to sodium is preferably 16 times or more, particularly preferably 40 times or more. A currently commercially available magnesium solution can be a magnesium solution (trade name: Ultra High Concentration Magnesium, available from NU SCIENCE) having magnesium:sodium=73:1.

The Mg:Na ratio in the water-soluble composition is preferably 16:1 to 73:1. When the composition contains magnesium at a high concentration, a sufficient amount of magnesium can be supplied to the mucosal tissues even under the environment where the composition is diluted. In addition, it is preferable to reduce the sodium content from the viewpoint of making it difficult to sense a salty taste when the composition is taken into the oral cavity.

The magnesium solution can be, for example, bittern, but it is considered that the content ratio between magnesium and sodium in the naturally derived bittern is not appropriate for improving the cellular environment. In general, it is known that bittern contains 18.84 g/100 ml magnesium chloride and 7.47 g/100 ml sodium chloride (Present and Future of "Bittern Industry" with Focus on Bromine, Bulletin of the Society of Sea Water Science, Japan, 1980, Vol. 34, No. 4, p. 217-23). The percentage content of the magnesium is about 5 w/v %, and the content ratio between magnesium and sodium is magnesium:sodium=1.63:1.

[Lactoferrin]

Lactoferrin can impart foaming properties to the water-soluble composition. By containing lactoferrin, the composition can remain in the mouth for a long time during brushing or gargling, which can enhance the absorption of the magnesium more effectively. The percentage content of the lactoferrin in the water-soluble composition is preferably 3.0 w/v % to 10.0 w/v %.

The lactoferrin is preferably lactoferrin in which a chelate structure is not formed, more preferably lactoferrin which can form a complex. Examples of preferred lactoferrin include lactoferrin with hollow lobes.

[Evaluation of Foaming Properties of Lactoferrin]

Predetermined amounts of lactoferrin were dissolved in purified water to increase the concentration of the lactoferrin in increments of 1.0 w/v %, thereby preparing 10 different preparations of the lactoferrin concentration of 1.0 w/v % to 10.0 w/v %. A predetermined amount of each preparation was put on a toothbrush (available from Lion Corporation, Clinica (registered trademark) Advantage NEXT STAGE toothbrush), and a mesh of a sieve was brushed by the toothbrush 200 times. Note that when the pressure during the brushing exceeds a certain level, the toothbrush makes a notification by sound and vibration. After brushing 200 times, the front and back sides of the sieve were observed to evaluate foaming properties.

Figure 2:
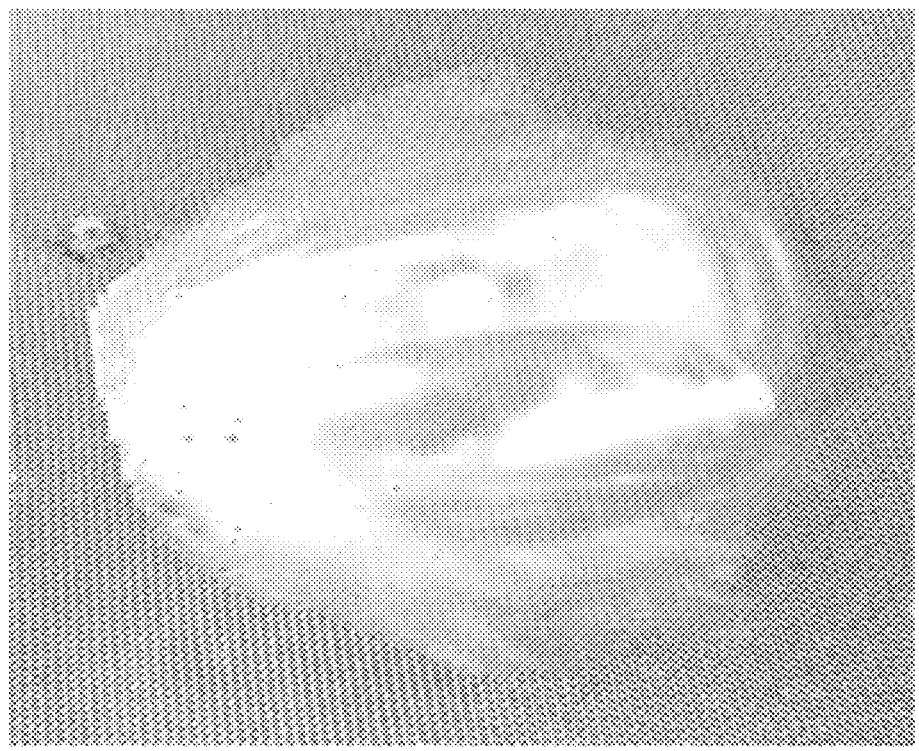
FIG. 2 is a photograph in foaming evaluation of a 3.0 w/v % lactoferrin preparation.

FIG. 1 is a photograph of the sieve after brushing 200 times using a 2.0 w/v % lactoferrin preparation. The preparations containing lactoferrin in an amount of 1.0 w/v % to 2.0 w/v % hardly foamed. FIG. 2 is a photograph of the sieve after brushing 200 times using a 3.0 w/v % lactoferrin preparation. Each preparation containing lactoferrin in an amount of 3.0 w/v % or more foamed well. It was considered that there was no change in the foaming effect even when the amount of lactoferrin added was more than 10.0 w/v %.

The lactoferrin used is preferably naturally derived lactoferrin. It is possible to constitute a composition with good foaming properties without using a foaming agent, such as a surfactant, and using only naturally derived ingredients by adding lactoferrin in an amount of 3.0 w/v % to 10.0 w/v % to the composition.

[Other Components]

The water-soluble composition can obtain various anti-inflammatory effects against bacterial inflammation by appropriately blending known components within a range not interfering with the effects of the present disclosure and employing various formulations. Thus, the composition may act as an auxiliary of dentifrices.

When the water-soluble composition is employed, for example, as an oral composition, the water-soluble composition can decrease the motility of bad bacteria in the mouth and improve the cellular environment on the gums, thereby making it possible to reduce inflammation and bleeding of the gums and prevent periodontal disease. Furthermore, the water-soluble composition has the possibility to reduce the risk of other diseases caused by bacteria passing through bloodstream to the whole body and causing periodontal disease. Specifically, the water-soluble composition has the possibility to reduce the risk of stroke, aspiration pneumonia, myocardial infarction, endocarditis, atherosclerosis, diabetes, low birth weight birth, and premature birth. Moreover, the high-concentration magnesium in the water-soluble composition is absorbed through the gastric mucosal tissue, which may contribute to normalization of damaged gastric mucosa. For example, the composition including the high-concentration magnesium is preferably supplied in the state where it is packed in plant-based capsules. The composition in this state has the possibility to decrease the risk of symptoms such as gastric ulcer, chronic gastritis, atrophic gastritis, and reflux esophagitis. When taken orally, the composition can reduce the motility of bad bacteria in the gastrointestinal tract, improve the cellular environment in the gastrointestinal tract, and improve constipation caused by a disorder in the balance between good and bad bacteria in the intestines. In addition, for example, the water-soluble composition can facilitate improvement of inflammation when it is applied to the wounded or burned skin.

While the water-soluble composition is applicable to applications other than those described above, the water-soluble composition is particularly suitable for oral compositions. When employed in, for example, a dentifrice among the oral compositions, the water-soluble composition may contain a flavoring agent, an abrasive, a humectant, a foaming agent, a thickener, a fragrance, a sweetener, a coloring agent, a preservative, a pH adjuster, an active ingredient, and the like and may be used as an auxiliary of the dentifrice.

When the water-soluble composition is used as an oral composition, the composition may contain a flavoring agent to mask bitter taste of magnesium. Examples of preferred flavoring agent include cyclodextrins. The cyclodextrins include α-cyclodextrin, β-cyclodextrin, and γ-cyclodextrin. One kind of the cyclodextrins may be blended alone, or two or more kinds of them may be blended appropriately in combination. In addition, another flavoring agent may be blended together with the cyclodextrins.

The abrasive can be, for example, one or more selected from the group consisting of silica-based abrasives such as silica gel, dibasic calcium phosphate dihydrate or anhydrous, tribasic calcium phosphate, calcium carbonate, aluminium hydroxide, alumina, magnesium carbonate, dimagnesium phosphate, trimagnesium phosphate, magnesium acetate, zeolite, hydroxyapatite, bentonite, synthetic resin, and other substances.

The humectant can be, for example, one or more selected from the group consisting of glycerin, sorbitol, ethylene glycol, propanediol, polyethylene glycol, 1,3-butylene glycol, propylene glycol, xylitol, maltitol, and other substances.

The foaming agent can be, for example, one or more selected from the group consisting of: anionic surfactants such as sodium lauryl sulfate, sodium tetradecenesulfonate, N-methyl-N-acyl taurine sodium salt, and N-methyl-N-acyl alanine sodium salt; and nonionic surfactants such as saccharose fatty acid ester, maltose fatty acid ester, maltitol fatty acid ester, lactitol fatty acid ester, sorbitan fatty acid ester, glycerin fatty acid ester, hexaglyceryl monolaurate, hexaglyceryl monomyristate, decaglyceryl monolaurate, polyoxyethylene sorbitan monolaurate, polyoxyethylene sorbitan monostearate, polyoxyethylene hardened castor oil, polyoxyethylene laurylether, and lauric acid diethanolamide.

The thickener can be, for example, one or more selected from the group consisting of guar gum, xanthan gum, karaya gum, carboxymethyl cellulose, hydroxylmethyl cellulose, colloidal magnesium aluminum silicate, and other substances.

The fragrance used can be, for example, a combination of known fragrance materials used in the oral composition such as natural fragrances such as a peppermint oil, a spearmint oil, an aniseed oil, an *eucalyptus* oil, a wintergreen oil, a *cassia* oil, a clove oil, a thyme oil, a sage oil, a lemon oil, a lime oil, an orange oil, a citrus oil, a *mentha* oil, a *cardamom* oil, a coriander oil, a mandarin oil, a lavender oil, a rosemary oil, a laurel oil, a chamomile oil, a caraway oil, a marjoram oil, a bay oil, a lemongrass oil, an *origanum* oil, a pine-needle oil, a neroli oil, a rose oil, a jasmine oil, a grapefruit oil, a sweety oil, and a Japanese citron oil.

Examples of the sweetener include xylitol, saccharin sodium, stevioside, and other substances.

Examples of the preservative include methylparaben, ethylparaben, propylparaben, butylparaben, parahydroxybenzoic acid, sodium benzoate, phenoxy ethanol, and other substances.

Examples of the pH adjuster include citric acid, phosphoric acid, malic acid, pyrophosphoric acid, lactic acid, tartaric acid, acetic acid, nitric acid, and other substances.

Examples of the active ingredient include: anti-inflammatory agents such as tranexamic acid, epsilon-aminocaproic acid, allantoin, glycyrrhetinic acid, and glycyrrhizic acid; plant extracts such as zeolite, azulene, dihydrocholesterol, chlorophyll, a Japanese *angelica* root extract, thyme, *Scutellaria* root, *Syzygium aromaticum* flower bud, and *Hamamelis*; vitamins; anti-tartar agents; anti-plaque agents; and the like. These active ingredients can be blended in an effective amount within a range not interfering with the effects of the present invention.

The water-soluble composition may further contain, as a useful ingredient, good bacteria such as lactic acid bacteria, *Bacillus subtilis* var *natto*, *Bacillus mesentericus*, and *Clostridium butyricum*. Specific examples of good bacteria include bacteria belonging to *Lactobacillus*, bacteria belonging to *Lactococcus*, and the like. Examples of the useful ingredient include: bifidobacteria such as *Bifidobacterium bifidum, Bifidobacterium longum, Bifidobacterium adolescentis, Bifidobacterium breve, Bifidobacterium infantis, Bifidobacterium animalis, Bifidobacterium pseudolongum*, and *Bifidobacterium lactis*; and lactic acid bacteria such as *Lactobacillus casei, Lactobacillus paracasei, Lactobacillus acidophilus, Lactobacillus reuteri, Lactobacillus gasseri, Lactobacillus bulgaricus, Lactobacillus salivarius, Lactobacillus rhamnosus, Lactobacillus plantarum*, and *Streptococcus thermophilus*. One kind of these useful ingredients may be used alone, or two or more kinds of them may be used in combination.

[Production Method]

Figure 3:
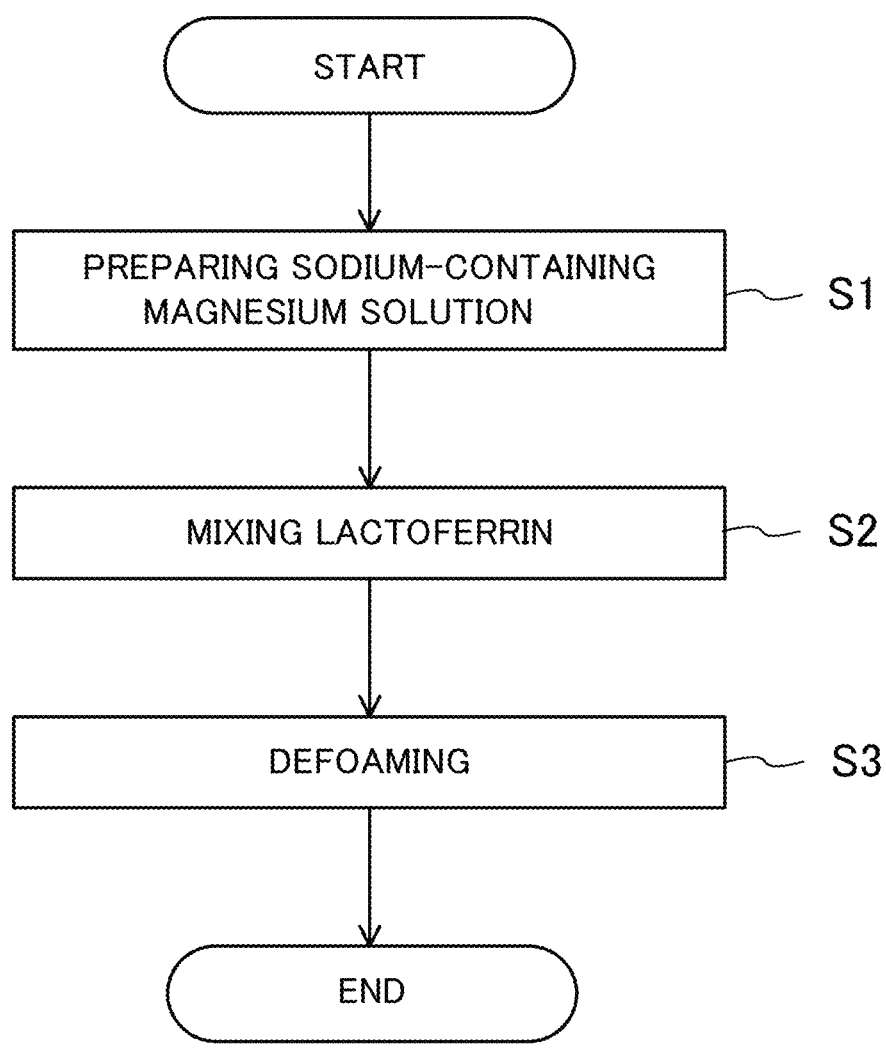
FIG. 3 is a flowchart showing an example of a production method of a water-soluble composition.

A production method of the water-soluble composition is conducted by the procedures shown in FIG. 3.

In the first step S1, a sodium-containing magnesium solution with a content ratio between the magnesium and the sodium of magnesium:sodium=16:1 to 73:1 is prepared. The sodium-containing magnesium solution used as a raw material is preferably a naturally derived magnesium solution produced from seawater or lake water of a salt lake.

In the second step S2, lactoferrin is mixed with the sodium-containing magnesium solution. The mixing is adjusted such that a mixture solution obtained has a percentage content of the magnesium of 2.0 w/v % to 12.0 w/v % and a percentage content of the lactoferrin of 3.0 w/v % to 10.0 w/v %. At this time, other ingredients such as an abrasive, a humectant, a foaming agent, a thickener, a fragrance, a sweetener, a flavoring agent, a colorant, a preservative, and active ingredients may be mixed together according to the use or formulation of the water-soluble composition.

In the third step S3, the mixture solution foamed due to the effect of lactoferrin is defoamed. Specifically, the defoaming is performed by a method in which the mixture solution is allowed to stand at ordinary temperature and ordinary pressure for a certain period of time (e.g., three days), a method in which the mixture solution is maintained in the cooling state at 0° C. to 5° C. and ordinary pressure for a certain period of time (e.g., three days), or a method in which the mixture solution is maintained at room temperature and pressure reduced to 0 atm for a certain period of time (5 hours to 24 hours).

The method for producing the water-soluble composition preferably does not further include adjusting the amount of sodium. Specifically, the method for producing the water-soluble composition more preferably does not further include adding sodium and/or removing sodium. That is, the Mg:Na ratio in the water-soluble composition is defined in the step S1. In other words, the first step S1 includes determining the content ratio between the magnesium and the sodium.

EXAMPLES

[Evaluation by Phase Contrast Observation]
The influence of the water-soluble composition on bacteria was evaluated using a phase contrast microscope. A specific evaluation method is as follows. A predetermined amount of plaque obtained from a dental patient was collected on slide glasses, and the solutions prepared with compositions shown in Table 1 below were added dropwise onto the respective slide glasses. A cover glass was placed on a specimen on the slide glass to obtain each sample. The sample obtained was observed for three minutes using a phase contrast microscope (P-SCOPE Pro, available from P-tech Co., ltd.).

Comparative Example 1

Figure 4:
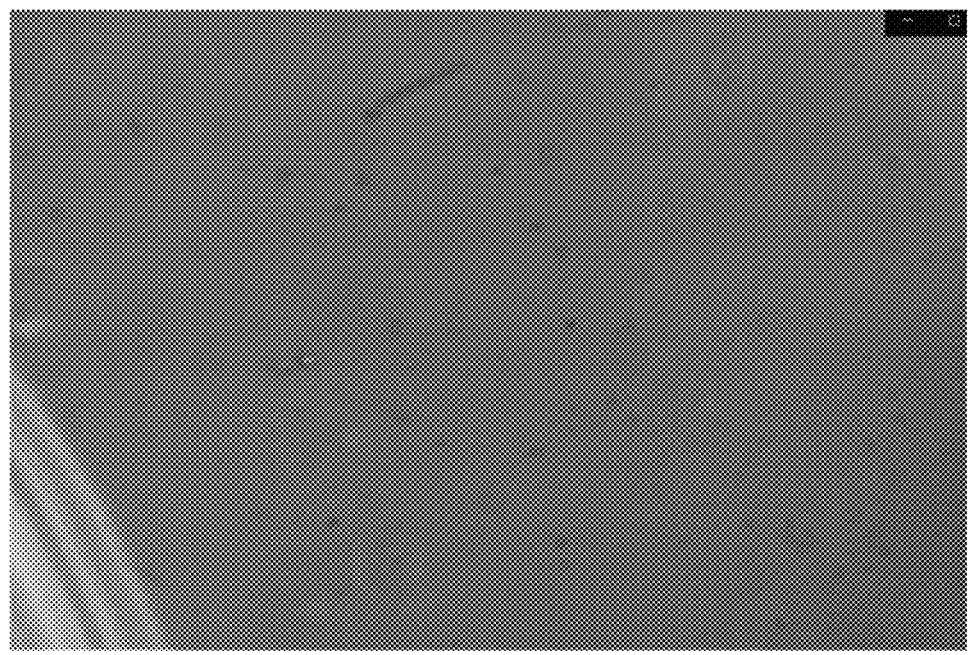
FIG. 4 is a photograph of Comparative Example 1 taken by a phase contrast microscope.

First, only the plaque was applied to a slide glass, a cover glass was placed thereon, and the sample was observed with a phase contrast microscope. FIG. 4 shows a photograph taken by the phase contrast microscope. In Comparative Example 1, a large number of bacteria moving actively were observed.

Example 1

Figure 5:
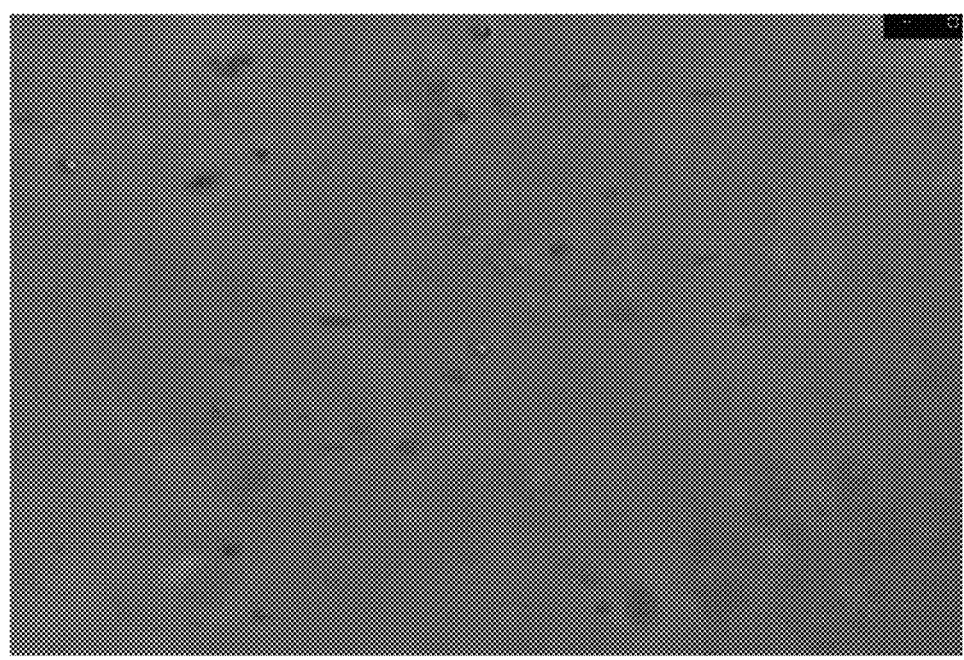
FIG. 5 is a photograph of Example 1, taken by a phase contrast microscope.

A water-soluble composition with a percentage content of magnesium of 10.5 w/v %, a percentage content of sodium of 0.25 w/v %, a percentage content of potassium of 1.18 w/v %, and a percentage content of lactoferrin of 4.5 w/v % (hereinafter also referred to as a specimen 1) was prepared. Specifically, first, a sodium-containing magnesium solution (MAGNEFORCE (registered trademark), available from MATIER Co., Ltd.) with a percentage content of magnesium of 10.5 w/v % and a Mg:Na ratio of 42.7:1 was provided. Then, 0.45 g of lactoferrin was mixed in 10 mL of the sodium-containing magnesium solution, thereby obtaining a mixture solution, which was a precursor of the specimen 1. Thereafter, the mixture solution was allowed to stand for three days at ordinary temperature and ordinary pressure to defoam, thereby preparing the specimen 1. FIG. 5 shows a photograph taken by the phase contrast microscope when the specimen 1 was added dropwise on the plaque. In Example 1, bacteria did not move at all, confirming that the specimen 1 was effective to suppress the function of bacteria.

Example 2

A specimen 1A was prepared in the same manner as in preparation of the specimen 1 except that 0.1 g of sodium chloride was further added to the sodium-containing magnesium solution (MAGNEFORCE (registered trademark), available from MATIER Co., Ltd.) to have a Mg:Na ratio of 16.4:1. The specimen 1A was added dropwise on the plaque and was observed with the phase contrast microscope. As in Example 1, bacteria did not move at all, confirming that the specimen 1A was effective to suppress the function of bacteria.

Comparative Example 2

14 mL of purified water was added to 16 mL of a sodium-containing magnesium solution (MAGNEFORCE (registered trademark), available from MATIER Co., Ltd.) with a percentage content of magnesium of 10.5 w/v % and a Mg:Na ratio of 42.7:1, and 0.11 g of sodium chloride was then added thereto. Thus, a specimen 2A with a percentage content of magnesium of 5.6 w/v % and a Mg:Na ratio of 20.3:1 was prepared. The specimen 2A was added dropwise on the plaque and was observed with the phase contrast microscope. As in Comparative Example 1, a large number of bacteria moving actively were observed.

Comparative Example 3

A specimen 2B with a Mg:Na ratio of 10.7:1 was prepared in the same manner as in preparation of the specimen 2A except that 0.15 g of sodium chloride was added instead of 0.11 g of sodium chloride. The specimen 2B was added dropwise on the plaque and was observed with the phase contrast microscope. As in Comparative Example 1, a large number of bacteria moving actively were observed.

Comparative Example 4

0.6 g of lactoferrin was mixed with 20 mL of commercially available bittern (trade name: "Hamamishio no Kaisuinigari" available from Hakumatsu Inc.) to prepare a specimen 2C. The specimen 2C had a percentage content of magnesium of 5.6 w/v %, a percentage content of lactoferrin of 3.0 w/v %, and a Mg:Na ratio of 1.3:1. The specimen 2C was added dropwise on the plaque and was observed with the phase contrast microscope. As in Comparative Example 1, a large number of bacteria moving actively were observed.

Comparative Example 5

0.75 g of lactoferrin was mixed with a solution obtained by diluting 10 mL of commercially available bittern (trade name: "Hamamishio no Kaisuinigari" available from Hakumatsu Inc.) with 15 mL of purified water to prepare a specimen 2D. The specimen 2D had a percentage content of magnesium of 2.2 w/v %, a percentage content of lactoferrin of 3.0 w/v %, and a Mg:Na ratio of 1.3:1. The specimen 2D was added dropwise on the plaque and was observed with the phase contrast microscope. As in Comparative Example 1, a large number of bacteria moving actively were observed.

Example 3

A specimen 3A with a percentage content of magnesium of 8.8 w/v %, a percentage content of lactoferrin of 3.9 w/v %, and a Mg:Na ratio of 47.7:1 was prepared using a sodium-containing magnesium solution (MAGNEFORCE (registered trademark), available from MATIER Co., Ltd.) and lactoferrin. The specimen 3A was added dropwise on the plaque and was observed with the phase contrast microscope. As in Example 1, bacteria were hardly moving, and bacteriostasis was observed.

Example 4

A specimen 3B with a percentage content of magnesium of 8.0 w/v %, a percentage content of lactoferrin of 3.5 w/v %, and a Mg:Na ratio of 47.4:1 was prepared using a sodium-containing magnesium solution (MAGNEFORCE (registered trademark), available from MATIER Co., Ltd.) and lactoferrin. The specimen 3B was added dropwise on the plaque and was observed with the phase contrast microscope. In Example 4, obvious bacteriostasis as in Examples 1 to 3 was not observed, but as compared with Comparative Examples 1 to 5, motility of bacteria was weakened, and it could be said that there was a tendency of bacteriostasis.

Table 1 shows the results of phase contrast observations of the specimens 1, 1A, 2A to 2D, and 3A and 3B. As can be seen from above, it was confirmed that the specimens 1, 1A, 3A, and 3B had a bacteriostatic effect.

TABLE 1

|  | Example 1 | Example 2 | Comparative Example 2 | Comparative Example 3 | Comparative Example 4 | Comparative Example 5 |
|---|---|---|---|---|---|---|
| Specimen name | Specimen 1 | Specimen 1A | Specimen 2A | Specimen 2B | Specimen 2C | Specimen 2D |
| Magnesium (w/v %) | 10.5 | 10.5 | 5.6 | 5.6 | 5.6 | 2.2 |
| Lactoferrin (w/v %) | 4.5 | 4.5 | 0 | 0 | 3.0 | 3.0 |
| Mg:Na ratio | 42.7:1 | 16.4:1 | 20.3:1 | 10.7:1 | 1.3:1 | 1.3:1 |
| Evaluation by phase contrast observation | Bacteriostatic | Bacteriostatic | No Bacteriostatic | No Bacteriostatic | No Bacteriostatic | No Bacteriostatic |

|  | Example 3 | Example 4 |
|---|---|---|
| Specimen name | Specimen 3A | Specimen 3B |
| Magnesium (w/v %) | 8.8 | 8.0 |
| Lactoferrin (w/v %) | 3.9 | 3.5 |
| Mg:Na ratio | 47.7:1 | 47.7:1 |
| Evaluation by phase contrast observation | Bacteriostatic | Bacteriostatic |

In the above Examples, the composition of a bacteriostatic water-soluble composition could be experimentally shown. From the above Examples, it is possible to suggest a preferred percentage content of magnesium for the effect of the water-soluble composition on suppressing activity of bacteria. However, the above experiments are not clinical trials. For example, if the water-soluble composition is used as a dentifrice, the water-soluble composition is mixed with saliva in the oral cavity of the user, and exhibits various improving effects on the affected area. The results of the following clinical trials are more important as a basis for the preferred composition of the water-soluble composition.

Next, the water-soluble composition of the present disclosure used as an oral composition, specifically a dentifrice, was evaluated for its effect by both subjective evaluation and objective evaluation.

[Subjective Evaluation]

17 test subjects were recruited, and asked to use the water-soluble composition of the present disclosure as a dentifrice for three months. The test subjects were instructed to swallow the water-soluble composition as much as possible without spitting out gargle water during brushing as much as possible. The test subjects evaluated the following ten items of the subjective evaluation with an integer of 0 to 10 before the start of the test and after three months. For example, for each item, "strongly felt" or "very applicable" is 10 points, and "not felt at all" or "not applicable at all" is 0 points.

Annoyed by bad breath
Stickiness and sliminess
Teeth wobble
Loose tooth, difficulty in chewing hard food
Poor gum color
Gums sometimes swell
Bleeding gum
Gingival recession
Increase in gap between teeth
Repeated stomatitis As an example entry of a check sheet of the subjective evaluation, evaluation results of the test subject 007 are shown in FIG. 6. For some items, the score after three months was less than that before the start of the test, and the symptoms were improved.

The evaluation results of the test subjects 001 to 017 are shown in Table 2.

TABLE 2

| Test Subject |  | 001 | 002 | 003 | 004 |
|---|---|---|---|---|---|
| Dentifrice used before test |  | I | I | I | I |
| Water-soluble composition | Magnesium (w/v %) | 2.0 | 10.5 | 10.5 | 10.5 |
|  | Lactoferrin (w/v %) | 3.2 | 4.5 | 4.5 | 4.5 |
|  | Mg:Na ratio | 42.7:1 | 42.7:1 | 42.7:1 | 42.7:1 |
| Subjective Evaluation | Bad breath | A | A | A | B |
|  | Stickiness and sliminess | A | A | A | B |
|  | Teeth wobble | C | C | B | C |
|  | Loose tooth, difficulty in chewing hard food | C | C | A | B |
|  | Gum color | C | C | B | C |
|  | Gingival swelling | A | B | B | C |
|  | Bleeding gum | A | B | A | C |
|  | Gingival recession | C | C | A | B |
|  | Gap between teeth | C | C | A | B |
|  | Frequency of stomatitis | A | C | B | C |
| Test Subject |  | 005 | 006 | 007 | 008 |
| Dentifrice used before test |  | I | I | XI | II |
| Water-soluble composition | Magnesium (w/v %) | 10.5 | 10.5 | 10.5 | 10.5 |
|  | Lactoferrin (w/v %) | 4.5 | 4.5 | 4.5 | 4.5 |
|  | Mg:Na ratio | 42.7:1 | 42.7:1 | 42.7:1 | 42.7:1 |
| Subjective Evaluation | Bad breath | B | A | B | C |
|  | Stickiness and sliminess | B | A | C | B |
|  | Teeth wobble | C | A | C | B |

TABLE 2-continued

| | | | | | | |
|---|---|---|---|---|---|---|
| | Loose tooth, difficulty in chewing hard food | C | A | C | | B |
| | Gum color | C | A | B | | B |
| | Gingival swelling | C | C | C | | A |
| | Bleeding gum | C | C | B | | B |
| | Gingival recession | B | A | C | | B |
| | Gap between teeth | B | C | C | | B |
| | Frequency of stomatitis | C | C | A | | A |

| Test Subject | | 009 | 010 | 011 | 012 | 013 |
|---|---|---|---|---|---|---|
| Dentifrice used before test | | III | IV | V | VI | VII |
| Water-soluble composition | Magnesium (w/v %) | 10.5 | 10.5 | 10.5 | 10.5 | 10.5 |
| | Lactoferrin (w/v %) | 4.5 | 4.5 | 4.5 | 4.5 | 4.5 |
| | Mg:Na ratio | 42.7:1 | 42.7:1 | 42.7:1 | 42.7:1 | 42.7:1 |
| Subjective Evaluation | Bad breath | B | A | B | A | B |
| | Stickiness and sliminess | B | A | A | A | C |
| | Teeth wobble | C | C | C | C | C |
| | Loose tooth, difficulty in chewing hard food | C | C | C | C | B |
| | Gum color | C | A | C | C | A |
| | Gingival swelling | C | A | C | B | A |
| | Bleeding gum | A | A | B | A | A |
| | Gingival recession | B | A | C | A | C |
| | Gap between teeth | B | A | C | A | C |
| | Frequency of stomatitis | B | B | B | C | A |

| Test Subject | | 014 | 015 | 016 | 017 |
|---|---|---|---|---|---|
| Dentifrice used before test | | VIII | IX | — | X |
| Water-soluble composition | Magnesium (w/v %) | 10.5 | 10.5 | 10.5 | 10.5 |
| | Lactoferrin (w/v %) | 4.5 | 4.5 | 4.5 | 4.5 |
| | Mg:Na ratio | 42.7:1 | 42.7:1 | 42.7:1 | 42.7:1 |
| Subjective Evaluation | Bad breath | A | A | C | C |
| | Stickiness and sliminess | A | A | C | C |
| | Teeth wobble | A | A | C | C |
| | Loose tooth, difficulty in chewing hard food | A | A | C | C |
| | Gum color | A | A | C | C |
| | Gingival swelling | A | A | C | C |
| | Bleeding gum | A | C | C | C |
| | Gingival recession | A | A | C | C |
| | Gap between teeth | A | A | C | C |
| | Frequency of stomatitis | C | A | C | C |

Dentifrices I to XI used before the test, shown in Table 2, are as follows. The symbol "-" indicates that the dentifrice was not used, i.e., the test subject brushed their teeth with water.

Dentifrice I: Magnesium toothpaste available from NU SCIENCE, containing magnesium chloride (MgCl·6H$_2$O), having a percentage content of magnesium chloride of 1.8 w/v %, converted from the content of magnesium, and containing no sodium and lactoferrin.

Dentifrice II: ClearClean (registered trademark) premium whitening, available from Kao Corporation.

Dentifrice III: New Aquafresh (registered trademark) ZF3, available from GSK plc.

Dentifrice IV: Ora2 (registered trademark) premium stain clear, available from Sunstar Inc.

Dentifrice V: Kamutect (registered trademark) complete care EX, available from GSK plc.

Dentifrice VI: Shabondama Soap (registered trademark) toothpaste, available from Shabondama Soap Co., Ltd.

Dentifrice VII: ClearClean (registered trademark) RR, available from Kao Corporation.

Dentifrice VIII: GUM (registered trademark) dental paste GS, available from Sunstar Inc.

Dentifrice IX: Shouyaku Hc, available from Kobayashi Pharmaceutical Co., Ltd.

The dentifrices II to IX contain neither magnesium nor lactoferrin.

Dentifrice X: B+, available from AT-MARK CONSUL., mainly containing fossil coral. Since natural fossil coral has a percentage content of magnesium of less than 1% according to known analysis examples, the toothpaste X is considered to have a percentage content of magnesium of less than 1 w/v %. The dentifrice X contains no lactoferrin.

Dentifrice XI: DENTOR SYSTEMA (registered trademark) EXW, available from Lion Corporation. The dentifrice XI contains neither magnesium nor lactoferrin.

The test subject 001 used a water-soluble composition having a percentage content of magnesium of 2.0 w/v %, a percentage content of lactoferrin of 3.2 w/v %, and a Mg:Na ratio of 42.8:1 (hereinafter, referred to as a specimen 4). The test subjects 002 to 017 used the specimen 1 of Example 1.

In Table 2, for ratings A through C, a symptom improvement of three or more points after three months from the start of the test was indicated as A, a symptom improvement of one to two points was indicated as B, and no change was indicated as C.

Before the test, the test subject 001 has been using a dentifrice I containing 1.8 w/v % magnesium and containing neither lactoferrin nor sodium. After three months from the start of the test, the test subject 001 answered that symptoms such as bad breath, stickiness and sliminess, swelling and bleeding of the gum, and stomatitis were greatly improved. The result demonstrated that the water-soluble composition containing sodium and lactoferrin in addition to magnesium improved the cellular environment in the oral cavity.

The test subjects 016 and 017 answered that no change was felt, while the other test subjects answered that symptoms were improved for many items.

Figure 7:
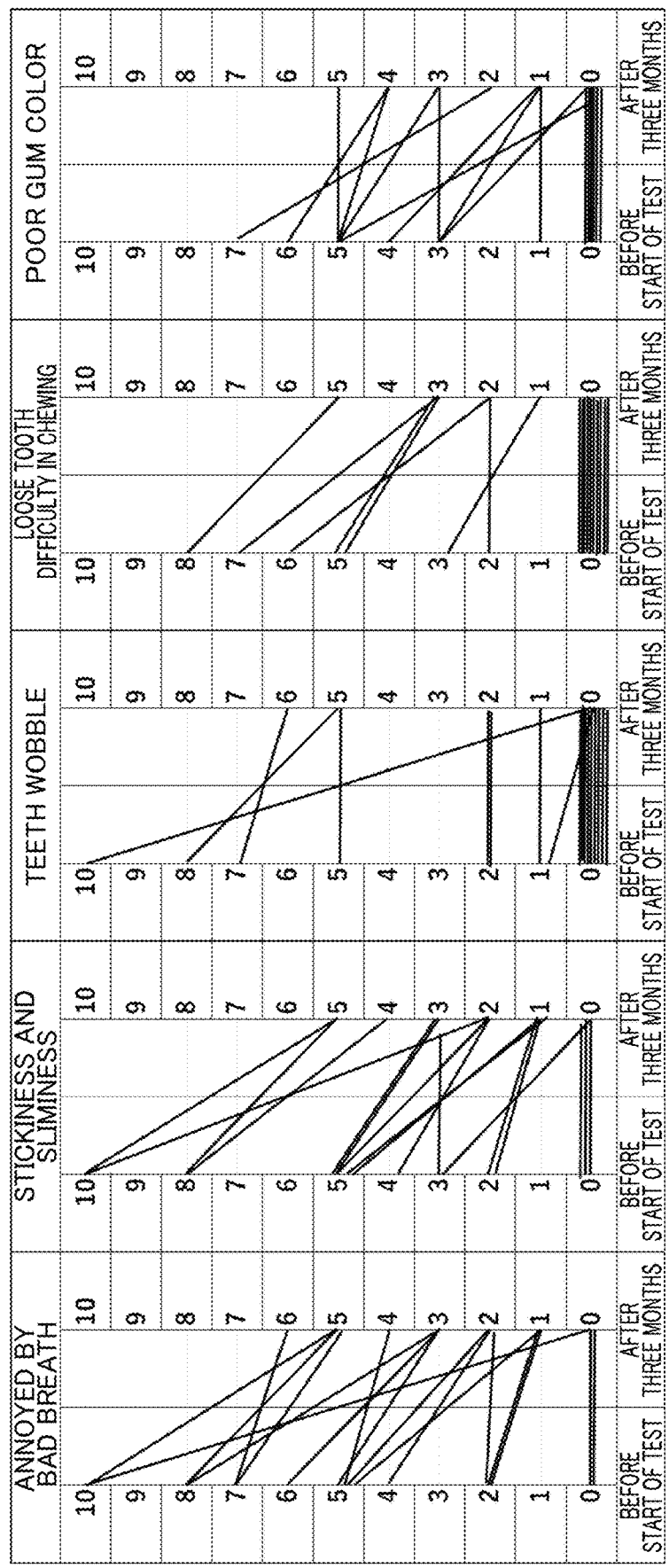
FIG. 7 is a graph showing changes in subjective evaluation before the start of the test and after three months.
Figure 8:
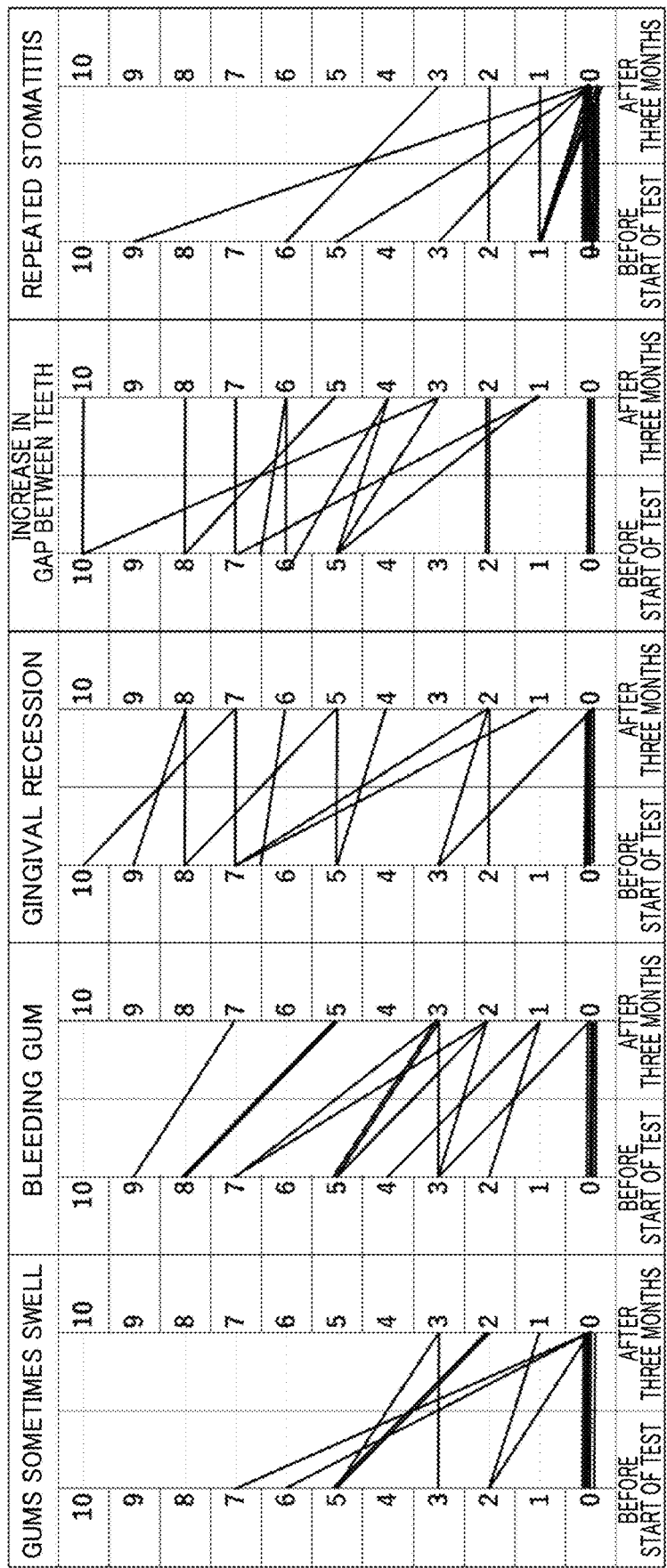
FIG. 8 is another graph showing changes in subjective evaluation before the start of the test and after three months.

FIGS. 7 and 8 are graphs of the results of the subjective evaluation of 17 test subjects, showing the change in score before the start of the test and after three months. In Table 2, an improvement of 3 points or more is defined as A. FIGS. 7 and 8 show that there were many test subjects who felt a large improvement of 8 to 10 points.

Table 3 shows the results of the subjective evaluation of 17 test subjects, specifically, results of the improvement rate calculated based on the change in score before the start of the test and after three months, and results of the increase rate of the number of test subjects who felt improvement based on the change in the number of test subjects who made an evaluation of 5 points or less.

TABLE 3

| | Before start of test Score | After three months Score | Improvement rate % | Before start of test The number of test subjects with score of 5 or less | After three months The number of subjects with score of 5 or less | Increase rate % |
|---|---|---|---|---|---|---|
| Annoyed by bad breath | 86 | 43 | 50 | 6 | 13 | 217 |
| Stickiness and sliminess | 75 | 33 | 44 | 8 | 15 | 188 |
| Teeth wobble | 36 | 21 | 58 | 13 | 14 | 108 |
| Loose tooth, difficulty in chewing hard food | 36 | 19 | 53 | 12 | 16 | 133 |
| Poor gum color | 47 | 24 | 51 | 11 | 16 | 145 |
| Gums sometimes swell | 45 | 18 | 40 | 11 | 16 | 145 |
| Bleeding gum | 69 | 37 | 54 | 9 | 15 | 167 |
| Gingival recession | 81 | 57 | 71 | 7 | 10 | 143 |
| Increase in gap between teeth | 88 | 62 | 71 | 5 | 11 | 220 |
| Repeated stomatitis | 30 | 6 | 20 | 14 | 17 | 121 |

Also from the improvement rate and the increase rate of the number of subjects who felt improvement, it was demonstrated that the water-soluble composition of the present disclosure had the effect of adjusting the cellular environment in the oral cavity.

[Objective Evaluation]

Some of the 17 test subjects were subjected to objective evaluation by the same practitioner before and after the test in a dental clinic. Specifically, a probing inspection was performed to check the periodontal pocket depth and the presence or absence of bleeding.

Figure 9:
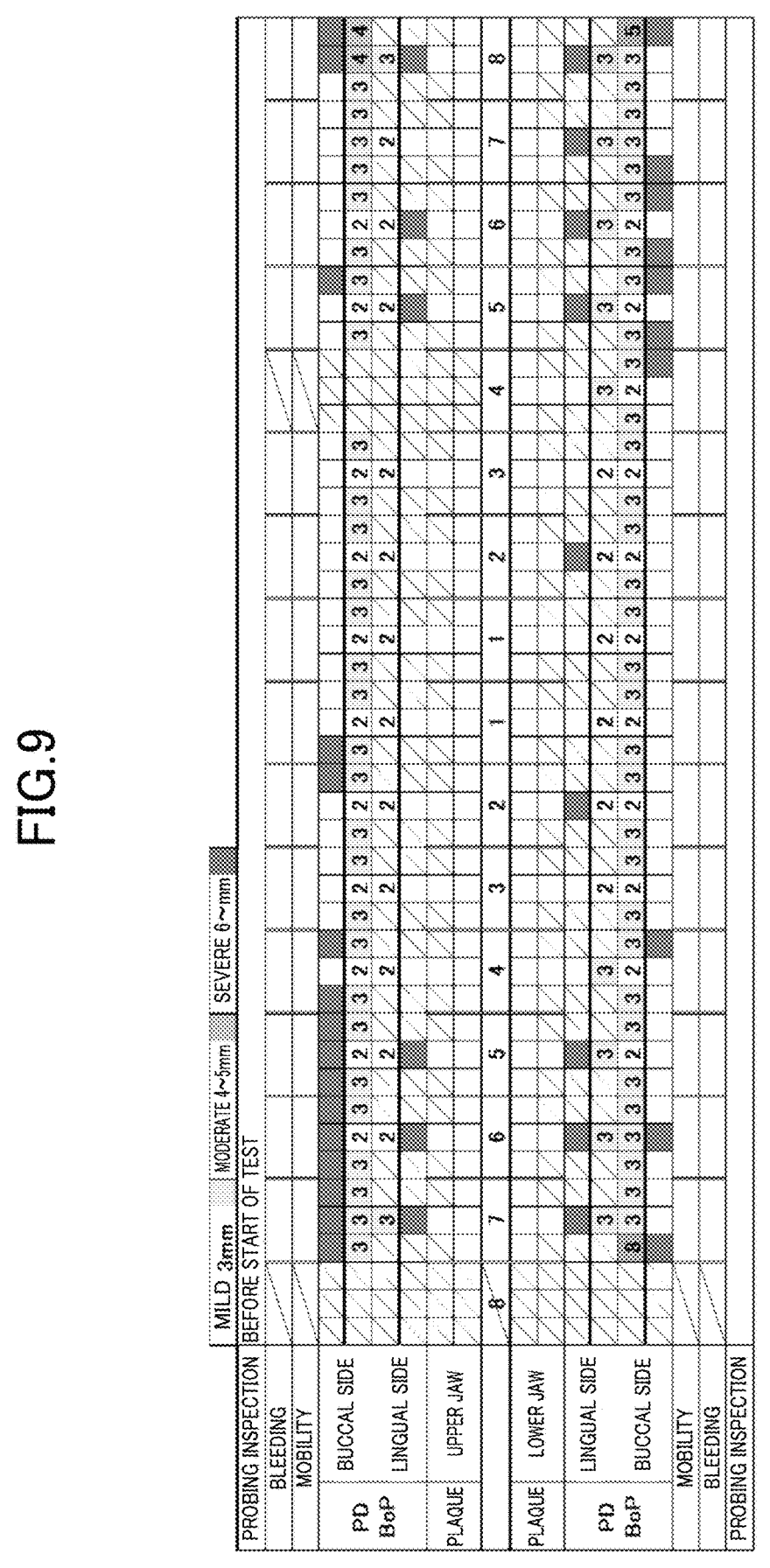
Figure 10:
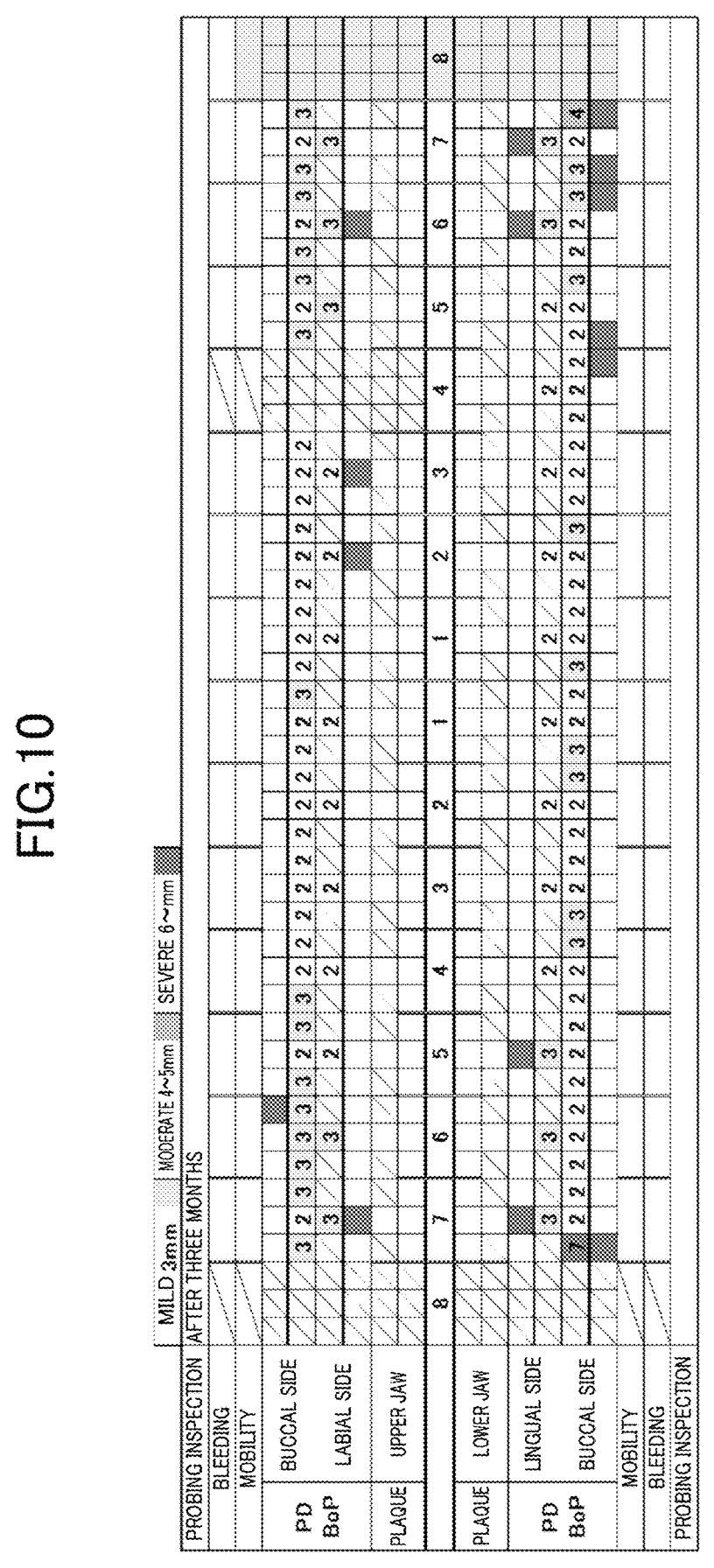

For the probing inspection, inspection tables shown in FIGS. 9 and 10 were used. In FIGS. 9 and 10, the term "PD" indicates the periodontal pocket depth (probing depth). The periodontal pocket depth was measured by inserting a periodontal pocket probe into the gingival crevice at the front and back of all teeth and visually checking the depth of probe insertion when the tip reached the bottom of the gingival crevice. In FIGS. 9 and 10, numerical values indicate measurement results (unit: mm) of the periodontal pocket depth.

In general, it is considered that the condition of the gum is good when the periodontal pocket depth is up to 1 mm in the center portions of teeth and is up to 2 mm in portions between teeth. The periodontal pocket depth of 3 mm is diagnosed as mild periodontal disease, that of 4 mm to 5 mm is diagnosed as moderate periodontal disease, and that of 6 mm or more is diagnosed as severe periodontal disease. As illustrated in FIGS. 9 and 10, in the inspection tables, the numerical values indicating the measurement results of the periodontal pocket depth are color-coded for mild, moderate, and severe symptoms.

In FIGS. 9 and 10, the term "BoP" indicates the inspection of the presence or absence of bleeding in the probing inspection (Bleeding on Probing), and the areas where bleeding was observed are indicated by colored cells above and below the measurement values of the periodontal pocket depth. The measurement of the periodontal pocket depth is an important clinical trial, and if bleeding is observed at a measurement site during the measurement of the periodontal pocket depth, it means that inflammation is occurring at the site. After the measurement of the periodontal pocket depths at the front and back of all teeth, the periodontal pocket probe was taken out, and whether there was bleeding from the gingival crevice was visually observed. As illustrated in FIGS. 9 and 10, in the inspection tables, a portion where bleeding was observed was colored. That is, it is considered that there is inflammation in the gingiva at the colored portion in the inspection tables. A value obtained by dividing the number of inspected sites at which bleeding was observed during the probing inspection by the total number of inspected sites, and expressed as a percentage, is referred to as the "BoP rate." When the BoP rate is significant, it can be said that the periodontal disease tends to progress, and it is said by the Japan Society of Periodontal Disease that the BoP rate is desirably 10% or less.

Table 4 shows the results of the probing inspection performed on seven test subjects out of 17 test subjects, before the start of the test and after three months. In Table 4, the "improvement rate of periodontal pocket depth" is a numerical value obtained by dividing the number of inspected sites with shallower periodontal pocket depth after three months than that before the start of the test by the total number of inspected sites and expressing the obtained value as a percentage. In Table 4, the "improvement in BoP rate" is a numerical value obtained by subtracting the BoP rate after three months from the BoP rate before the start of the test. The "improvement rate of periodontal pocket depth" and the "improvement in BoP rate" both indicate that the larger the numerical value is, the more the improvement is.

TABLE 4

|  |  | Test Subject | | | | | | |
|---|---|---|---|---|---|---|---|---|
|  |  | 001 | 007 | 008 | 010 | 015 | 016 | 017 |
| Dentifrice used before test | | I | XI | II | IV | IX | — | X |
| Water-soluble composition | Magnesium (w/v %) | 2.0 | 10.5 | 10.5 | 10.5 | 10.5 | 10.5 | 10.5 |
| | Lactoferrin (w/v %) | 3.2 | 4.5 | 4.5 | 4.5 | 4.5 | 4.5 | 4.5 |
| | Mg:Na ratio | 42.7:1 | 42.7:1 | 42.7:1 | 42.7:1 | 42.7:1 | 42.7:1 | 42.7:1 |
| Objective evaluation | Periodontal pocket depth Improvement rate | 12% | 34% | 37% | −7% | 1% | 25% | 0% |
| | Improvement in BoP rate | −1% | 22% | 6% | 10% | 12% | 21% | 5% |

Among the test subjects who used the specimen 1, those who showed improvement in periodontal pocket depth (test subjects 007, 008, and 016) showed high improvement rates of 25% to 39%. The test subject 001 who used the specimen 4 also showed improvement in periodontal pocket depth, but showed a lower improvement rate than those of the test subjects 007, 008, and 016. In addition, the test subjects who used the specimen 1 showed overall improvement in BoP rate.

The test subjects 016 and 017 answered that they did not feel any improvement in the subjective evaluation, but improvements were observed in the objective evaluation. Specifically, the test subject 016 showed significant improvement in both periodontal pocket depth and BoP rate, and the test subject 017 showed improvement in BoP rate. The test subject 016 had a BoP rate of 92.9% before the start of the test and had many portions with periodontal pocket depths of 4 mm or more, and thus had a mild to moderate periodontal disease. This is considered to be the reason that the improvement effect was remarkably observed in the test subject 016. The test subject 017 had a BoP rate of 5.4% before the start of the test and had no portion with a periodontal pocket depth of 4 mm or more, and thus was in a good oral environment. It is therefore considered that although there was no remarkable change, the oral environment was further improved.

Based on the results of the objective evaluation, it is found that the periodontal pocket depth can be improved when the percentage content of magnesium content is 2.0 w/v % in the water-soluble composition of the present disclosure applied as an oral composition. It is also considered that if the percentage content of magnesium content is 10.5 w/v % or more, the periodontal pocket depth and the BoP rate can be more effectively improved.

In addition to the 17 test subjects, nine test subjects were allowed to use the specimen 1 as a dentifrice for three months. After three months from the start of the test, a total of 26 test subjects were allowed to freely answer not only a change in the oral cavity but also a change in physical condition or the like as feeling of use of the water-soluble composition of the present disclosure.

As a result, four out of 26 test subjects answered that "constipation was ameliorated." It is considered that the cellular environment in the oral cavity was improved by the water-soluble composition of the present disclosure, thereby improving the cellular environment in the gastrointestinal tract and bacterial constipation. The results show that the cellular environment in the gastrointestinal tract is improved when the water-soluble composition of the present disclosure is orally ingested.

One test subject said, "Before the test began, I had a tooth covering removed and was in pain. I couldn't go to a dentist after that, but after applying the specimen 1 to the affected area for 10 days, the pain subsided." Another test subject said, "I had swollen lips due to allergy, but the symptom improved with the use of the specimen 1." These statements indicate that the specimen 1 has an anti-inflammatory effect in the oral cavity.

When a test subject X applied the specimen 1 to a burned wound, the symptom of the burn improved more quickly than in the case where the specimen 1 was not applied.

A test subject X dropped one drop of the specimen 1 into each of the left and right eyes. In addition, a test subject Y prepared a solution of two drops of the specimen 1 in 2.5 ml of water and washed his/her eyes with the resultant solution. For the test subjects X and Y, the discomfort due to eye discharge and the discomfort due to dry eyes disappeared after the instillation or the eye washing. This result indicates that the specimen 1 is suitable for use as an eye drop, an artificial tear, an eyewash, and a contact lens insertion agent.

A test subject impregnated several drops of the specimen 1 in a cotton swab and applied the specimen 1 to the ear canal. Inflammation caused by scratch of the external ear was subsided after 48 hours, from which it is considered that the bacterial balance in the ear canal was improved.

A test subject applied, to his/her skin, a solution obtained by dropping 0.2 ml of the specimen 1 into approximately 1.5 ml of a commercially available lotion. After eight hours, the skin surface film and/or the cornified layer of the skin were smoothened.

A test subject applied an excessive amount of a solution obtained by diluting the specimen 1 two-fold to a portion of the calf convulsing so as to be transdermally absorbed. After eight hours, the muscle tension of the calf was relieved, and the pain was improved.

The specimen 1 can be packed in capsules and used as a suppository, which is expected to induce defecation, reduce bleeding around the anus, improve hemorrhoid symptoms, and improve the bacterial balance in the rectum. When a test subject Z used a suppository which is the specimen 1 packed in a capsule, bleeding due to ulcerative colitis was suppressed. A test subject Z packed the specimen 1 into a plant-based capsule and took 2 ml each of the specimen 1 on his/her empty stomach continuously. A few months later, it was observed that HbA1c value of blood test was improved. Therefore, it is considered that gastric erosion, that is, damages of gastric mucosal tissue may be improved. In addition, animals such as dogs and cats continued to take drinking water obtained by adding one drop of the water-soluble composition into 100 to 200 ml of water approximately for one month. As a result, the bad breath of animals ameliorated.

The specimen 1 can be diluted and used as a nasal lavage fluid or nasal drops, and is expected to ameliorate inflammation of the nasal mucosa, improve sinusitis, and improve the bacterial balance in the nasal cavity.

When used as a dentifrice, the water-soluble composition can be expected to be effective for amelioration of stomatitis, amelioration of pain in the covered part of teeth, prevention of drying in the oral cavity, amelioration of bad breath, amelioration of sore lips, amelioration of swelling of lips, and amelioration of headache. When used as a topical agent, the water-soluble composition can also be expected to be effective for amelioration of sinusitis, amelioration of itching of the skin, moisturizing of the skin, prevention of dandruff of the scalp, amelioration of sunburn, amelioration of sore of the nipple, and the like. When used as an internal agent, the water-soluble composition can also be expected to be effective for amelioration of hemorrhoid.

As can be seen from above, the water-soluble composition is useful particularly as an oral composition, and is also useful in other applications.

The invention claimed is:

1. A water-soluble composition for bacteriostasis or for absorption through mucosal tissue, the composition comprising:
    magnesium; sodium; and protein,
    a content ratio between the magnesium and the sodium being magnesium:sodium=16:1 to 73:1,
    the protein being lactoferrin,
    a percentage content of the magnesium being 8.0 w/v % to 12.0 w/v %,
    a percentage content of the lactoferrin being 3.0 w/v % to 10.0 w/v %.

2. The water-soluble composition for bacteriostasis or for absorption through mucosal tissue according to claim 1, wherein
    the percentage content of the magnesium is 10.5 w/v % to 12.0 w/v %, and
    the water-soluble composition is for oral use.

3. A method for producing the water-soluble composition for bacteriostasis or for absorption through mucosal tissue according to claim 1, the method comprising:
    preparing a sodium-containing magnesium solution with a content ratio between the magnesium and the sodium of magnesium:sodium=16:1 to 73:1;
    mixing lactoferrin and the sodium-containing magnesium solution to obtain a mixture solution with a percentage content of the magnesium of 8.0 w/v % to 12.0 w/v % and a percentage content of the lactoferrin of 3.0 w/v % to 10.0 w/v %; and
    defoaming the mixture solution.

* * * * *